(12) United States Patent
Wu et al.

(10) Patent No.: US 11,666,676 B1
(45) Date of Patent: Jun. 6, 2023

(54) AROMA DEVICE FOR SELF-GENERATING WATER VAPOR

(71) Applicant: Xinmin Wu, Guangdong (CN)

(72) Inventors: Xinmin Wu, Guangdong (CN); Xianjun Xie, Guangdong (CN)

(73) Assignee: Shenzhen Laowu Mifang Biotechnology Co., Ltd., Shenzhen (CN)

( * ) Notice: Subject to any disclaimer, the term of this patent is extended or adjusted under 35 U.S.C. 154(b) by 0 days.

(21) Appl. No.: 17/731,707

(22) Filed: Apr. 28, 2022

Related U.S. Application Data (63) Continuation of application No. PCT/CN2022/087840, filed on Apr. 20, 2022.

(51) Int. Cl.
*A61L 9/03* (2006.01)

(52) U.S. Cl.
CPC ........... *A61L 9/03* (2013.01); *A61L 2209/133* (2013.01)

(58) Field of Classification Search
CPC .............................. A61L 9/03; A61L 2209/133
See application file for complete search history.

(56) References Cited

U.S. PATENT DOCUMENTS

| | | | |
|---|---|---|---|
| 4,171,340 A * | 10/1979 | Nishimura | A61L 9/03 422/1 |
| 5,416,931 A | 5/1995 | Wolfenden et al. | |
| 6,548,015 B1 * | 4/2003 | Stubbs | A61L 9/02 422/123 |
| 7,815,878 B1 | 10/2010 | Wheatley | |
| 10,182,961 B2 | 1/2019 | Whittier | |
| 10,278,893 B2 | 5/2019 | Parker | |
| 11,147,738 B1 | 10/2021 | Nunez et al. | |
| 2002/0148911 A1 | 10/2002 | Beck et al. | |
| 2005/0031511 A1 * | 2/2005 | Nohara | A61L 9/015 422/123 |
| 2007/0257383 A1 * | 11/2007 | Chan | F24F 6/04 261/107 |
| 2016/0205892 A1 | 7/2016 | Hills | |
| 2021/0283365 A1 | 9/2021 | Meyer et al. | |
| 2022/0047467 A1 | 2/2022 | Ingham | |

\* cited by examiner

*Primary Examiner* — Sean E Conley
*Assistant Examiner* — Brendan A Hensel (57) ABSTRACT

The invention provides an aroma device for self-generating water vapor. The aroma device comprises a water vapor generator and an aroma body bearing portion. The water vapor generator is internally provided with a self-heating bag that is chemically reacted with water to generate high-temperature water vapor. Generated water vapor with aroma escapes outwards through an aroma carrier. The aroma device is convenient to carry and wide in diffusion range without a power supply. The high-temperature water vapor directly gasifies essence in a medium without generating other harmful dust and smog, and the aroma effect is remarkably enhanced.

11 Claims, 7 Drawing Sheets

AROMA DEVICE FOR SELF-GENERATING WATER VAPOR

CROSS REFERENCE TO RELATED APPLICATION

This application is a continuation of International Patent Application No. PCT/CN2022/087840, filed on Apr. 20, 2020, and the entire contents of which are incorporated herein by reference.

FIELD OF TECHNOLOGY

The present invention relates to the field of aroma devices, and particularly to an aroma device for self-generating water vapor.

BACKGROUND

Aroma having a history of many years in China not only can improve the environmental sanitation, remove odors and the like, but also can help people relieve pressure, insomnia, headache and the like. Aroma devices in the prior art mainly include combustion type aroma devices, naturally volatilized aroma devices and ultrasonic atomization type aroma devices. The combustion type aroma devices, for example, sandalwood and aromatherapy candle, feature high diffusion speed and lasting fragrance but will generate smog or harmful substances in combustion processes to affect air quality, and if they are used improperly, potential safety hazards will be generated. For the naturally volatilized aroma devices, an aroma liquid product is attached to aroma carriers such as rattans and flowers and plants, and fragrance is diffused by natural volatilization. Compared with the combustion type aroma devices, the naturally volatilized aroma devices are more persistent in fragrance but feature slow natural volatilization speed and small diffusion range. Substances such as alcohol as volatilizers are combustibles which are inconveniently carried and have certain potential safety hazards. For the ultrasonic atomization type aroma devices, water molecules and dissolved aroma liquid are decomposed into nanoscale cold fog with a diameter of 0.1-5 microns by means of vibration of an ultrasonic nebulizer, and the nanoscale cold fog is diffused to surrounding air, so that the ultrasonic atomization type aroma devices are conveniently used. However, the generated cold fog is not active enough in molecular movement, and essence is not gasified completely, so that the ultrasonic atomization type aroma devices feature low diffusion speed and small range.

SUMMARY

The present invention is intended to provide an aroma device for self-generating water vapor. The aroma device is convenient to carry and wide in diffusion range without a power supply. The high-temperature water vapor directly gasifies essence in a medium without generating other harmful dust and smog, and the atomized essence and water vapor together diffused to air will be attached to wall spaces and other furniture and clothes more effectively, so that the aroma effect is remarkably enhanced.

In order to achieve the above-mentioned objective, the present invention provides a technical scheme as follows: an aroma device for self-generating water vapor includes a water vapor generator including a reaction tank body and a self-heating bag, wherein the self-heating bag is arranged in a tank body of the reaction tank body, the reaction tank body includes a water inlet and a water vapor outlet, the water inlet is used for introducing water into the reaction tank body, the self-heating bag is chemically reacted with water entering the reaction tank body via the water inlet to generate high-temperature water vapor, and the water vapor outlet is used for outwards escaping of the water vapor from the reaction tank body; and an aroma body bearing portion including a water vapor inlet and a water vapor escape port, wherein the water vapor inlet is communicated with the water vapor outlet; the aroma body bearing portion internally includes essence or essential oil and an aroma carrier containing the essence or the essential oil, water vapor generated in the water vapor generator passes through the water vapor outlet, the water vapor inlet and the aroma carrier in sequence, and finally, water vapor carrying aroma escapes outwards from the water vapor escape port.

Further, the outer side of the aroma body bearing portion is further provided with a barrier net, and the barrier net is arranged at a position, close to the water vapor escape port, at the other end of the aroma carrier, and is used for preventing an external fixed impurity from polluting an interior of the aroma body bearing portion.

Further, the water vapor generator and the aroma body bearing portion are integrally arranged, the aroma body bearing portion is arranged above the reaction tank body, the water vapor generated in the reaction tank body passes through the aroma carrier carrying essence, then the water vapor then passes through the barrier net, and finally, the water vapor carrying aroma escapes outwards from the water vapor escape port.

Further, the water vapor escape port on an outer side of the barrier net is further provided with an easy open end, and the easy open end is fixedly connected with a side wall of the reaction tank body.

Further, the water vapor generator further includes a water bath body that is a container for containing water; and the water inlet is formed at a bottom of the reaction tank body, the water inlet in the bottom of the reaction tank body is capable of being immersed into water of the water bath body, and the self-heating bag and water are subjected to a chemical exothermic reaction.

Further, the water vapor generator and the aroma body bearing portion are capable of being separately arranged, the aroma body bearing portion is placed at an opening above the reaction tank body, and the self-heating bag is arranged in the reaction tank body.

Further, the water vapor inlet is formed in a bottom of the aroma body bearing portion, and the water vapor in the reaction tank body passes through the water vapor inlet, the aroma carrier and the barrier net in sequence and finally escapes outwards from the water vapor escape port.

Further, the aroma body bearing portion is a cone section with a bottom diameter smaller than a top diameter, and the bottom of the aroma body bearing portion is placed at the opening above the reaction tank body.

Further, the aroma carrier is a sponge body or cotton.

It can be known by analysis that the aroma device for self-generating water vapor disclosed by the present invention has the following beneficial effects:

1. The heating bag is reacted with water to release heat, and aroma molecules are diffused to air as the high-temperature water vapor passes through the aroma body to achieve an aroma purpose. In the using process, no naked fire is generated, and it is unnecessary to connect the power supply, so that it is safer; and moreover, the aroma device disclosed by the present invention is concise in structure and convenient to carry.

2. Calcium oxide in the heating bag is reacted with water to generate calcium hydroxide and release a lot of heat, the generated calcium hydroxide is reacted with sodium hydroxide in the heating bag and powdered aluminum again to generate calcium tetrahydroxyaluminate, aluminum hydroxide and hydrogen, and meanwhile, in the reaction process, heat will be released continuously, and a duration of the heat release process is prolonged.

3. Compared with the prior art, no naked fire is generated in the using process of the present invention, so that it is relatively safe. The aroma body is heated by the high-temperature water vapor, and the aroma molecules are diffused outwards to air by the high-temperature water vapor and are attached to surfaces of surfaces of indoor objects such as walls or furniture, so that fragrance is more lasting.

4. The technical scheme of the present invention reduces the operating difficulty of adding water into the aroma device, decreases the water changing time and consumables and saves the cost as well.

BRIEF DESCRIPTION OF THE DRAWINGS

The drawings of the description constituting a part of the disclosure are to provide further understanding of the present invention. The schematic embodiment and description thereof are used for explaining the present invention and do not limit the present invention improperly. In the drawings.

DESCRIPTION OF NUMERALS IN DRAWINGS:

1-reaction tank body; 2-aroma body bearing portion; 3-self-heating bag; 4-easy open end; 5-barrier net; 6-water bath body; 7-water; 21-aroma carrier; 101-water inlet; 102-water vapor outlet; 103-water vapor inlet; 104-escape port.

DETAILED DESCRIPTION OF THE EMBODIMENTS

Detail description on the present invention will be made below in combination with the drawings and the embodiments. Each example is provided by the present invention in an explained manner rather than limits the present invention. Modifications and variations on the present invention can be made without departing the scope or the spirit of the present invention.

In description of the present invention, orientation or position relationships indicated by terms: 'inner', 'outer', 'front', 'back', 'left', 'right', 'vertical', 'horizontal', 'top', 'bottom' and the like are orientation or position relationships indicated by the drawings and are only to describe the present invention and simplify the description rather than indicates or implies that the indicated device or components must have specific orientations. Therefore, it cannot be construed as limitations to the present invention. Terms 'connecting', 'connection' and 'arrange' used in the present invention should be understood in a broad sense, for example, 'connecting', 'connection' and 'arrange' can be either fixed connection or detachable connection; and can be either directly connection or connection via intermediate parts. Those of ordinary skill in the art can understand specific meanings of the terms according to specific conditions.

An aroma device for self-generating water vapor includes a water vapor generator and an aroma body bearing portion 2. The water vapor generator includes a reaction tank body 1 and a self-heating bag 3. The self-heating bag 3 is arranged in a tank body of the reaction tank body 1, and the self-heating bag 3 is chemically reacted with water 7 entering the reaction tank body 1 via the water inlet 101 to generate high-temperature water vapor. The self-heating bag 3 includes the following compositions in percent by weight: 24-46% of powdered aluminum, 19-44% of calcium oxide, 4-11% of sodium hydroxide, 1-2% of powdered coke, 2-5% of activated carbon, 1-3% of sodium hydride, 2-5% of calcined diatomite and 2-4% of a zeolite powder. Chemical equations between powdered aluminum and water, between calcium oxide and water and between sodium hydroxide and water in the components of the self-heating bag are as follows:

$$CaO+H_2O=Ca(OH)_2$$

$$Ca(OH)_2+2Al+2H_2O=Ca[Al(OH)_4]_2+H_2\uparrow$$

$$2Al+2H_2O+2NaOH=2NaAlO_2+3H_2\uparrow$$

$$Na_H+H_2O=NaOH+H_2\uparrow$$

The reaction tank body 1 includes a water inlet 101 and a water vapor outlet 102, the water inlet 101 is used for introducing water into the reaction tank body 1, and the water vapor outlet 102 is used for outwards escaping of the water vapor from the reaction tank body 1. Water vapor generated by the above-mentioned chemical equations enters the aroma body bearing portion 2 via the water vapor outlet 102.

An aroma body bearing portion 2 includes a water vapor inlet 103 and a water vapor escape port 104, wherein the water vapor inlet 103 is communicated with the water vapor outlet 102; water vapor enters into the aroma body bearing portion 2 via the water vapor outlet 102 and the water vapor inlet 103. The aroma body bearing portion 2 internally includes essence or essential oil and an aroma carrier 21 containing the essence or the essential oil, wherein the aroma carrier 21 is a sponge body or cotton.

Water vapor generated in the water vapor generator passes through the water vapor outlet 102, the water vapor inlet 103 and the aroma carrier 21 in sequence, and finally, water vapor carrying aroma escapes outwards from the water vapor escape port 104. The outer side of the aroma body bearing portion 2 is further provided with a barrier net 5. The barrier net 5 is arranged at a position, close to the water vapor escape port 104, at the other end of the aroma carrier 21, and the barrier net 5 is used for preventing an external fixed impurity from polluting an interior of the aroma body bearing portion 2.

EXAMPLE 1

Figure 1:
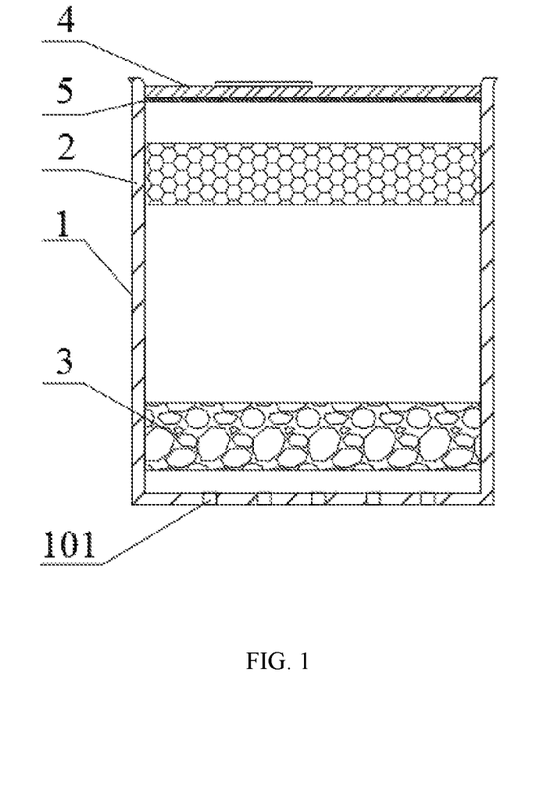
FIG. 1 is a structural schematic diagram of reaction tank body of an embodiment I of the present invention.
Figure 2:
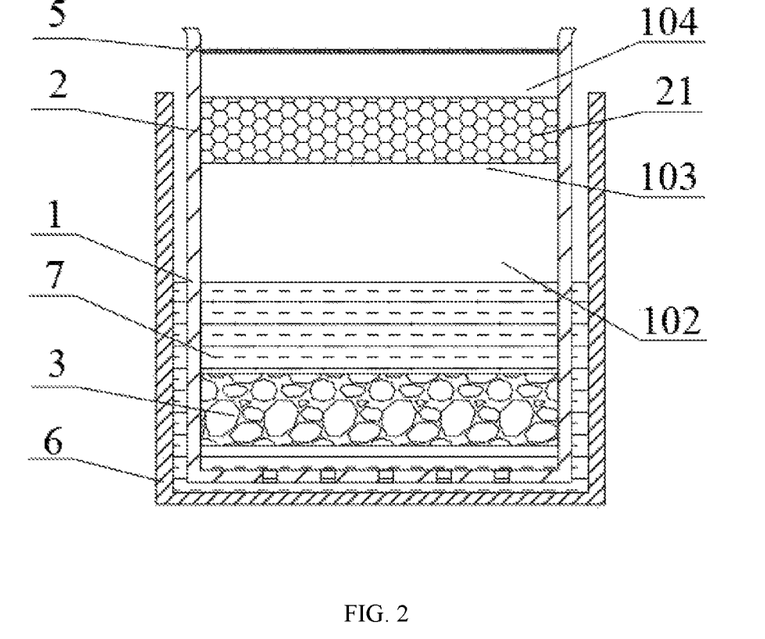
FIG. 2 is a structural schematic diagram of use of an aroma device in a water adding state of an embodiment I of the present invention.

As shown in FIG. 1 to FIG. 2, an aroma device for self-generating water vapor provided by the present invention includes a water vapor generator which further includes a reaction tank body 1. The reaction tank body 1 is cylindrical, an upper opening in the reaction tank body 1 is provided with an easy open end 4, and the easy open end 4 is fixedly connected with a side wall of an edge of a top of the reaction tank body 1. During use, the easy open end 4 is lifted upwards to open the reaction tank body 1.

A barrier net 5 is arranged below the easy open end 4 in the reaction tank body 1, the barrier net 5 is fixedly connected with the side wall of the reaction tank body 1, and the barrier net 5 is used for separating an interior of the reaction tank body 1 from an outside so as to prevent an impurity from entering the reaction tank body 1 to pollute the aroma carrier 21. A bottom of the reaction tank body 1 is provided with a water inlet 101, and the water inlet 101 is communicated with the outside. The water vapor generator further includes a water bath body 6, and the water bath body 6 is a container for containing water; and the water inlet 101 formed at a bottom of the reaction tank body 1 is capable of being immersed into the water 7 of the water bath body 6, and the self-heating bag 3 and water are subjected to a chemical exothermic reaction.

The self-heating bag provided by the embodiment 1 included the following compositions in percent by weight: 40% of powdered aluminum, 38% of calcium oxide, 11% of sodium hydroxide, 1% of powdered coke, 5% of activated carbon, 1% of sodium hydride, 2% of calcined diatomite and 2% of a zeolite powder. The compositions were mixed and crushed into a 100-mesh powder, and the mixed powder per 40 g was put in a non-woven fabric package. These additives: powdered coke, activated carbon, sodium hydride, calcined diatomite and zeolite powder play a major role of adsorbing water. Before the self-heating bag is used, it can play a moistureproof role, so that the period of validity of the self-heating bag is prolonged, and the using effect is prevented from being affected as calcium oxide is affected with damp to react.

When the self-heating bag is used for heating aroma, each of the self-heating bags is in full contact with 230 g of water. In the reaction process, calcium oxide is chemically reacted with water to generate calcium hydroxide and a lot of heat is released. Meanwhile, both the generated calcium hydroxide and sodium hydroxide are capable of being chemically reacted with powdered aluminum to generate calcium tetrahydroxyaluminate, aluminum hydroxide and hydrogen, and meanwhile, in the reaction process, heat will be released continuously. In the reaction process, the inner temperature can reach up to 260° C. maximally, the highest temperature of the released water vapor can reach up to 160° C., and a time of continuous escaping of water vapor in the reaction process is longer than 10 min.

The water vapor generator and the aroma body bearing portion 2 are integrally arranged, the aroma body bearing portion 2 is arranged above the reaction tank body 1, the water vapor generated in the reaction tank body 1 passes through the aroma carrier 21 carrying essence, then the water vapor then passes through the barrier net 5, and finally, the water vapor carrying aroma escapes outwards from the water vapor escape port 104.

When the bottom of the reaction tank body 1 is immersed into the water 7, the water 7 enters into the reaction tank body 1 via the water inlet 101 and is chemically reacted with the self-heating bag 3 to generate heat, thus, high-temperature water vapor is released to the aroma body. In the heating process, no naked fire is generated, so that it is safer. After the water vapor passes through the aroma body bearing portion 2, the aroma molecules are blended with the water vapor, and the water vapor carrying aroma is diffused to air. The temperature of the water vapor is higher compared with that of cold fog, so that water molecules are more active and larger in diffusion range. Moreover, the diffused water vapor carrying the aroma molecules is diffused to air, and is easily attached to the surfaces of objects such as wall spaces or furniture, so that indoor fragrance is more lasting.

A specific using mode of the embodiment is as follows: first, the easy pull end 4 at the top of the reaction tank body 1 is lifted upwards, the tank body of the reaction tank body 1 is opened, and then the bottom of the reaction tank body 1 is immersed into the water bath body 6 containing the water 7, wherein the weight of the water contained in the water bath body 6 is about 5 times of that of the self-heating bag 3. After the bottom of the reaction tank body is immersed into water, the water 7 is in contact reaction with the self-heating bag 3 at the bottom of the reaction tank body 1, so that essence of the aroma body bearing portion 2 is heated and escapes together with the water vapor towards air.

EXAMPLE 2

Figure 3:
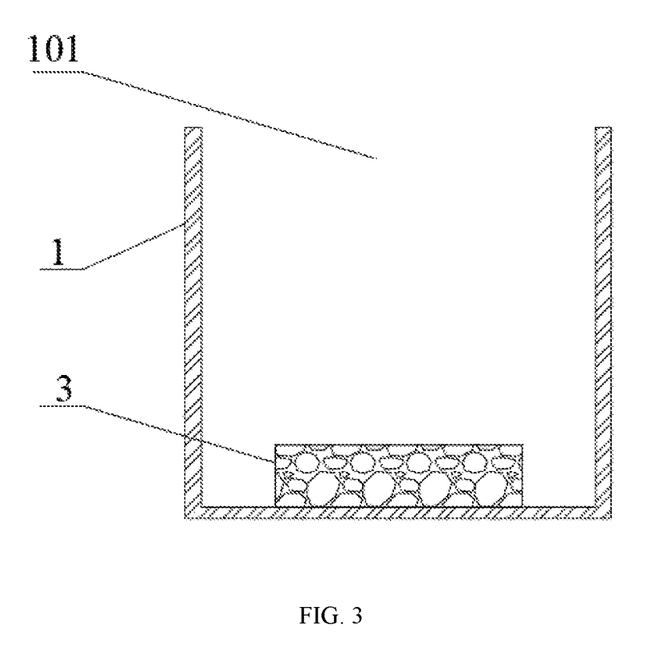
FIG. 3 is a structural schematic diagram of reaction tank body of an embodiment II of the present invention.
Figure 4:
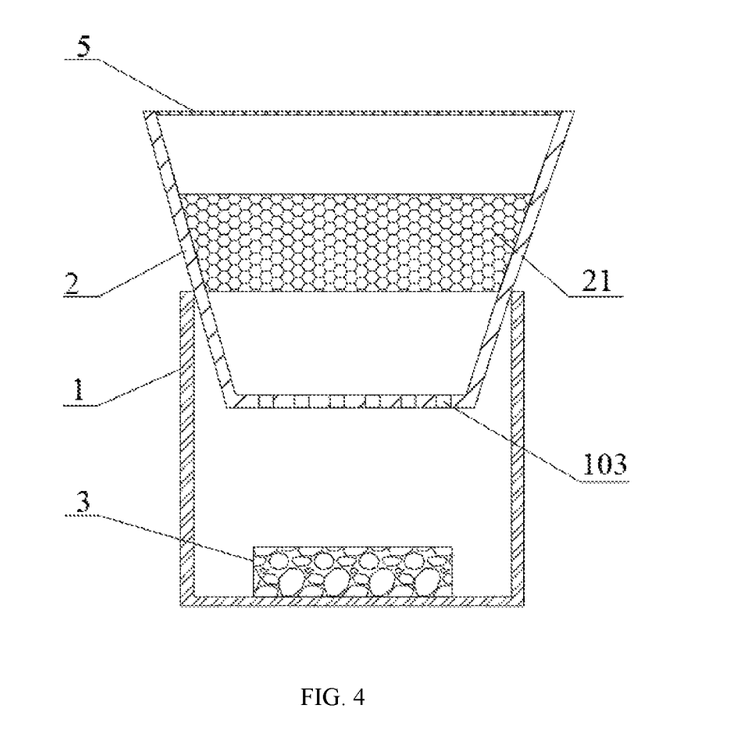
FIG. 4 is a structural schematic diagram of an aroma device in a non-water adding state of an embodiment II of the present invention.
Figure 5:
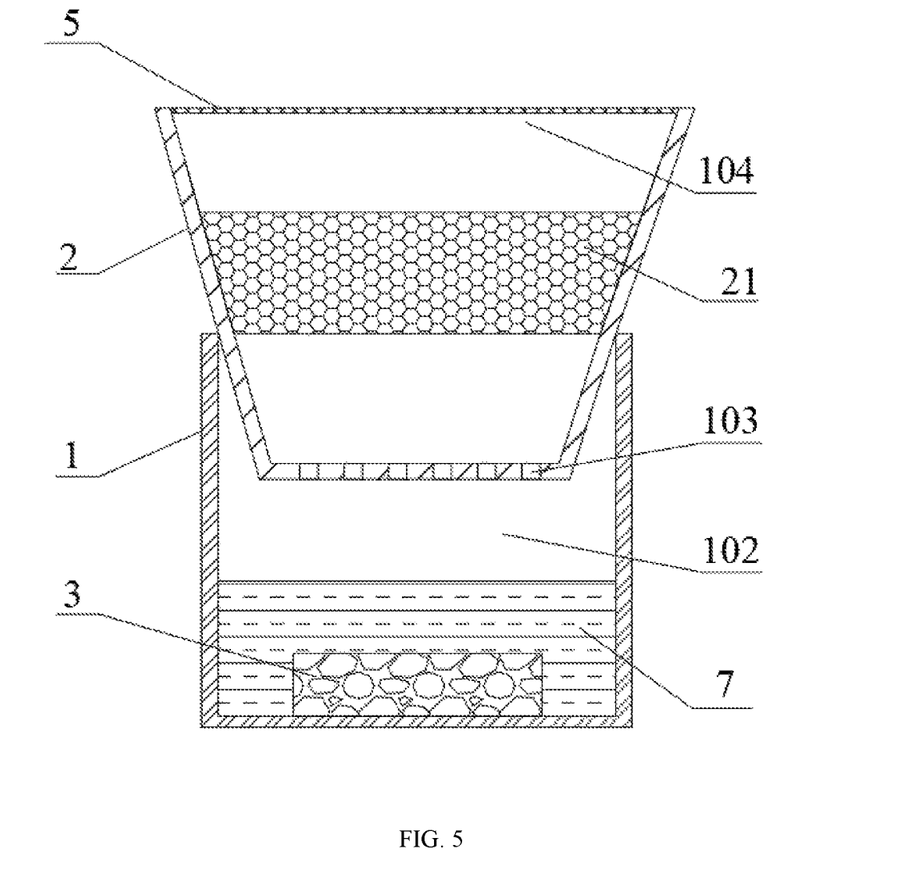
FIG. 5 is a structural schematic diagram of an aroma device in a water adding state of an embodiment II of the present invention.
Figure 6:
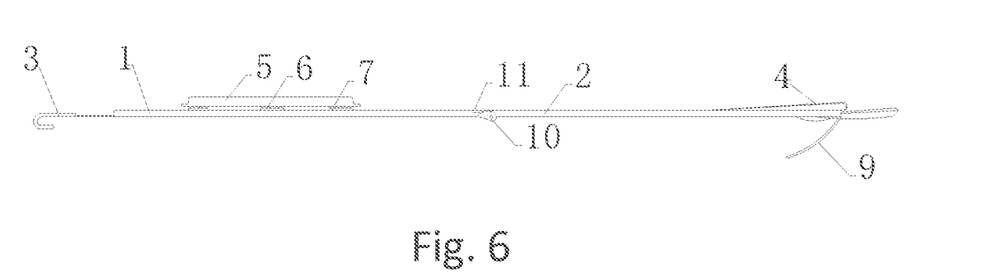
Figure 7:
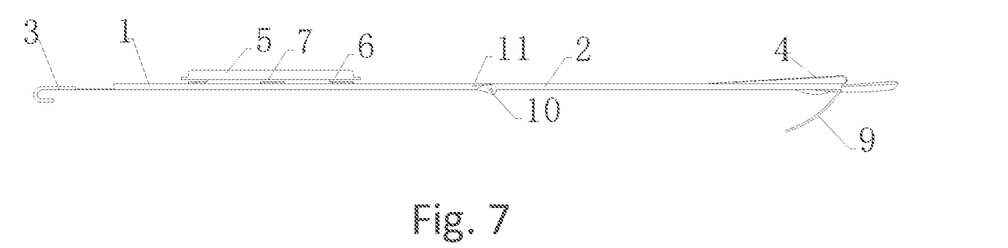
Figure 8:
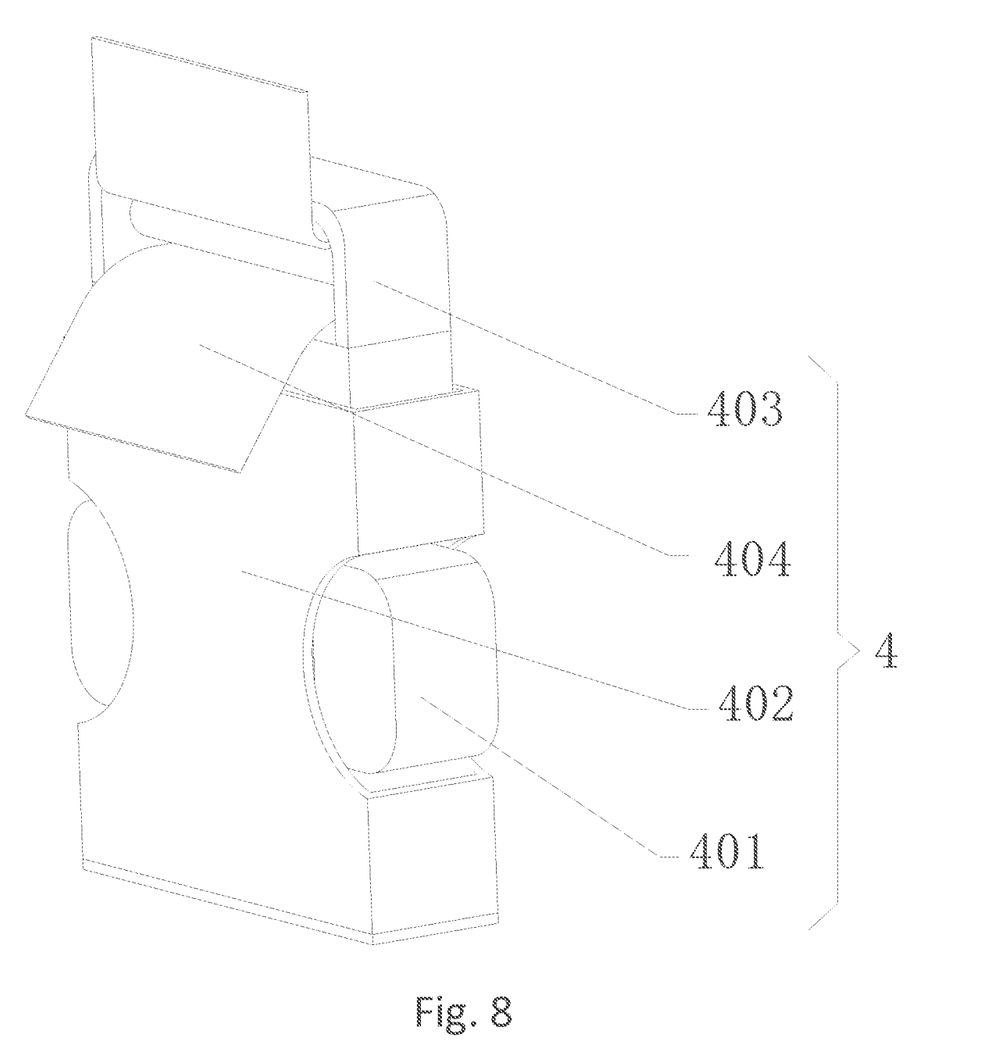

As shown in FIG. 3 to FIG. 5, an aroma device for self-generating water vapor provided by the present invention includes a reaction tank body 1 and an aroma body bearing portion 2. The aroma body bearing portion 2 is a cone section with a bottom diameter smaller than a top diameter, a barrier net 5 is arranged at an opening above the aroma body bearing portion 2, the barrier net 5 is fixedly connected with a side wall of the aroma body bearing portion 2, and the barrier net 5 is used for separating an interior of the reaction tank body 1 from an outside so as to prevent an impurity from entering the interior of the aroma body bearing portion 2 to pollute the aroma carrier. The bottom of the aroma body bearing portion 2 is provided with several water vapor inlets 103, thereby facilitating a communication between the interior of the aroma body bearing portion 2 and the reaction tank body 1.

The water vapor generator and the aroma body bearing portion 2 are capable of being separately arranged, the water vapor generator includes the reaction tank body 1, the reaction tank body 1 is a cylindrical tank body with an opening above, the aroma body bearing portion 2 is placed at the opening above the reaction tank body 1, and the self-heating bag 3 is arranged in the reaction tank body 1.

The water vapor inlets 103 are formed in a bottom of the aroma body bearing portion 2, and the water vapor in the reaction tank body 1 passes through the water vapor inlets 103, the aroma carrier 21 and the barrier net 5 in sequence and finally escapes outwards from the water vapor escape port 104.

During use, the aroma body bearing portion 2 is taken down from the water vapor generator first, water with the weight which is about 5 times of that of the self-heating bag 3 is added into the reaction tank body 1 of the water vapor generator, and then the cone section-shaped aroma body bearing portion 2 is placed on the reaction tank body 1. The self-heating bag 3 is reacted with the water to generate a lot of high-temperature water vapor, the high-temperature water vapor enters into the aroma body bearing portion 2 via the water vapor inlets 103, passes through the water vapor inlets 103, one end of the aroma carrier 21, the other end of the aroma carrier 21 and the barrier net 5 in sequence, and finally the water vapor carrying aroma escapes outwards from the water vapor escape port 104 and the aroma molecules are diffused to air.

The self-heating bag provided by the embodiment 2 included the following compositions in percent by weight: 35% of powdered aluminum, 38% of calcium oxide, 8% of sodium hydroxide, 2% of powdered coke, 5% of activated carbon, 3% of sodium hydride, 5% of calcined diatomite and 4% of a zeolite powder. The compositions were mixed and crushed into a 100-mesh powder, and the mixed powder per 40 g was put in a non-woven fabric package.

These additives: powdered coke, activated carbon, sodium hydride, calcined diatomite and zeolite powder play a major role of adsorbing water. Before the self-heating bag is used, it can play a moistureproof role, so that the period of validity of the self-heating bag is prolonged, and the using effect is prevented from being affected as calcium oxide is affected with damp to react.

When the self-heating bag is used for heating aroma, each of the self-heating bags is in full contact with 230 g of water. In the reaction process, calcium oxide is chemically reacted with water to generate calcium hydroxide and a lot of heat is released. Meanwhile, both the generated calcium hydroxide and sodium hydroxide are capable of being chemically reacted with powdered aluminum to generate calcium tetrahydroxyaluminate, aluminum hydroxide and hydrogen, and meanwhile, in the reaction process, heat will be released continuously. In the reaction process, the inner temperature can reach up to 260° C. maximally, the highest temperature of the released water vapor can reach up to 160° C., and a time of continuous escaping of water vapor in the reaction process is longer than 10 min.

It can be seen from the above-mentioned description that the above-mentioned embodiment of the present invention realizes the following technical effects: the heating bag is reacted with water to release heat, and aroma molecules are diffused to air as the high-temperature water vapor passes through the aroma body to achieve an aroma purpose. In the using process, no naked fire is generated, so that it is safer. The aroma device disclosed by the present invention is concise in structure and convenient to carry.

Calcium oxide in the heating bag provided by the present invention is reacted with water to generate calcium hydroxide and release a lot of heat, the generated calcium hydroxide is reacted with sodium hydroxide in the heating bag and powdered aluminum again to generate calcium tetrahydroxyaluminate, aluminum hydroxide and hydrogen, and meanwhile, in the reaction process, heat will be released continuously, and a duration of the heat release process is prolonged.

Compared with the prior art, no naked fire is generated in the using process of the present invention, so that it is relatively safe. The aroma body is heated by the high-temperature water vapor, and the aroma molecules are diffused outwards to air by the high-temperature water vapor and are attached to surfaces of surfaces of indoor objects such as walls or furniture, so that fragrance is more lasting.

The above is merely preferred embodiments of the present invention and is not used to limit the present invention. For those skilled in the art, various alternations and changes can be made on the present invention. Any modification, equivalent replacement, improvement, etc. made within the spirit and principle of the present invention shall be regarded as within the protection scope of the present invention.

What is claimed is:

1. An aroma device for self-generating water vapor, comprising: a water vapor generator comprising a reaction tank body and a self-heating bag, wherein the self-heating bag is arranged in a tank body of the reaction tank body, the reaction tank body comprises a water inlet and a water vapor outlet, the water inlet is configured to introduce water into the reaction tank body, the self-heating bag is chemically reacted with water entering the reaction tank body via the water inlet to generate water vapor, and the water vapor outlet is used for outwardly escaping of the water vapor from the reaction tank body; and an aroma body bearing portion comprising a water vapor inlet and a water vapor escape port, wherein the water vapor inlet is communicated with the water vapor outlet; the aroma body bearing portion internally comprises essence or essential oil and an aroma carrier containing the essence or the essential oil, the water vapor generated in the water vapor generator passes through the water vapor outlet, the water vapor inlet and the aroma carrier in sequence, and finally, water vapor carrying aroma escapes outwards from the water vapor escape port;

the self-heating bag comprises the following compositions in percent by weight: 24-46% of powdered aluminum, 19-44% of calcium oxide, 4-11% of sodium hydroxide, 1-2% of powdered coke, 2-5% of activated carbon, 1-3% of sodium hydride, 2-5% of calcined diatomite and 2-4% of zeolite powder.

2. The aroma device for self-generating water vapor according to claim 1, wherein an outer side of the aroma body bearing portion is further provided with a barrier net, and the barrier net is configured to prevent an external fixed impurity from polluting an interior of the aroma body bearing portion.

3. The aroma device for self-generating water vapor according to claim 2, wherein the water vapor generator and the aroma body bearing portion are integrally arranged, the aroma body bearing portion is arranged above the reaction tank body, the water vapor generated in the reaction tank body passes through the aroma carrier carrying essence, then the water vapor passes through the barrier net, and finally, the water vapor carrying aroma escapes outwards from the water vapor escape port.

4. The aroma device for self-generating water vapor according to claim 3, wherein the water vapor escape port on an outer side of the barrier net is further provided with an open end, and the open end is fixedly connected with a side wall of the reaction tank body.

5. The aroma device for self-generating water vapor according to claim 4, wherein the water vapor generator further comprises a water bath body that is a container for containing water; and the water inlet is formed at a bottom of the reaction tank body, the water inlet in the bottom of the reaction tank body is capable of being immersed into water of the water bath body, and the self-heating bag and water are subjected to a chemical exothermic reaction.

6. The aroma device for self-generating water vapor according to claim 2, wherein the water vapor generator and the aroma body bearing portion are capable of being separately arranged, the aroma body bearing portion is placed at an opening above the reaction tank body, and the self-heating bag is arranged in the reaction tank body.

7. The aroma device for self-generating water vapor according to claim 6, wherein the water vapor inlet is formed in a bottom of the aroma body bearing portion, and the water vapor in the reaction tank body passes through the water vapor inlet, the aroma carrier and the barrier net in sequence and finally escapes outwards from the water vapor escape port.

8. The aroma device for self-generating water vapor according to claim 7, wherein the aroma body bearing portion is a cone section with a bottom diameter smaller than a top diameter, and the bottom of the aroma body bearing portion is placed at the opening above the reaction tank body.

9. The aroma device for self-generating water vapor according to claim 2, wherein the aroma carrier is a sponge body or cotton.

10. The aroma device for self-generating water vapor according to claim 1, wherein the self-heating bag comprises the following compositions in percent by weight: 40% of powdered aluminum, 38% of calcium oxide, 11% of sodium hydroxide, 1% of powdered coke, 5% of activated carbon, 1% of sodium hydride, 2% of calcined diatomite and 2% of zeolite powder.

11. The aroma device for self-generating water vapor according to claim 1, wherein the self-heating bag comprises the following compositions in percent by weight: 35% of powdered aluminum, 38% of calcium oxide, 8% of sodium hydroxide, 2% of powdered coke, 5% of activated carbon, 3% of sodium hydride, 5% of calcined diatomite and 4% of zeolite powder.

* * * * *